United States Patent
Hartman et al.

(10) Patent No.: US 10,053,720 B2
(45) Date of Patent: Aug. 21, 2018

(54) VECTORS AND HOST CELLS COMPRISING A MODIFIED SV40 PROMOTER FOR PROTEIN EXPRESSION

(71) Applicant: ABBVIE BIOTHERAPEUTICS INC., Redwood City, CA (US)

(72) Inventors: Taymar E. Hartman, Redwood City, CA (US); J. Yun Tso, Menlo Park, CA (US); Yimin He, Union City, CA (US)

(73) Assignee: AbbView Biotherapeutics Inc., Redwood City, CA (US)

( * ) Notice: Subject to any disclaimer, the term of this patent is extended or adjusted under 35 U.S.C. 154(b) by 0 days.

(21) Appl. No.: 15/161,059

(22) Filed: May 20, 2016

(65) Prior Publication Data

US 2016/0265018 A1  Sep. 15, 2016

Related U.S. Application Data

(63) Continuation of application No. 14/361,684, filed as application No. PCT/US2011/062720 on Nov. 30, 2011, now abandoned.

(51) Int. Cl.

| | |
|---|---|
| *C12N 15/85* | (2006.01) |
| *C12P 21/00* | (2006.01) |
| *C07K 16/00* | (2006.01) |
| *C07K 14/005* | (2006.01) |
| *C07K 16/28* | (2006.01) |
| *C12N 7/00* | (2006.01) |

(52) U.S. Cl.
CPC ............ *C12P 21/00* (2013.01); *C07K 14/005* (2013.01); *C07K 16/00* (2013.01); *C07K 16/2896* (2013.01); *C12N 7/00* (2013.01); *C12N 15/85* (2013.01); *C07K 2317/14* (2013.01); *C07K 2317/51* (2013.01); *C07K 2317/515* (2013.01); *C12N 2710/22022* (2013.01); *C12N 2710/22043* (2013.01); *C12N 2800/107* (2013.01); *C12N 2800/24* (2013.01); *C12N 2830/20* (2013.01); *C12N 2830/60* (2013.01)

(58) Field of Classification Search
None
See application file for complete search history.

(56) References Cited

U.S. PATENT DOCUMENTS

| 5,827,705 A | 10/1998 | Dean |
| 9,260,528 B2 | 2/2016 | Hartman |
| 2010/0159489 A1 | 6/2010 | Klein et al. |
| 2011/0177600 A1 | 7/2011 | Rutter et al. |
| 2012/0301429 A1 | 11/2012 | Hartman et al. |
| 2014/0356351 A1 | 12/2014 | Greenberg |

FOREIGN PATENT DOCUMENTS

| EP | 0628639 A1 | 12/1994 |
| EP | 2385115 A1 | 11/2011 |
| WO | WO 2007/135515 A1 | 11/2007 |
| WO | WO 2009/003622 A1 | 1/2009 |

OTHER PUBLICATIONS

Fromm, M. et al., 1983, "Transcription in-Vivo from SV-40 Early Promoter Deletion Mutants Without Repression by Large T Antigen, " *J Molecular and Applied Genetics* 2(1):127-135.
Gorman, C. M. et. al., 1982, "Recombinant Genomes Which Express Chloramphenicol Acetyltransferasein Mammalian Cells," *Mol Cell Biol* 2(2): 1044-1051.
Huang et al., 2007, "An Efficient and Targeted Gene Integration System for High-Level Antibody Expression," *J Immunol Methods* 322 (1-2):28-39.
Sequence Alignment of Instant SEQ ID No. 1 with SEQ ID No. 1 of U.S. Pat. No. 5,827,705, conducted on Oct. 21, 2015, 2 pages.

*Primary Examiner* — Channing S Mahatan
(74) *Attorney, Agent, or Firm* — Dechert LLP

(57) ABSTRACT

The present disclosure is directed to expression vectors, comprising a weakened SV40 promoter, and recombinant mammalian cells capable of producing high levels of a polypeptide of interest, methods of generating and using such recombinant mammalian cells.

19 Claims, 12 Drawing Sheets

SEQ ID NO:1

Figure 2A:
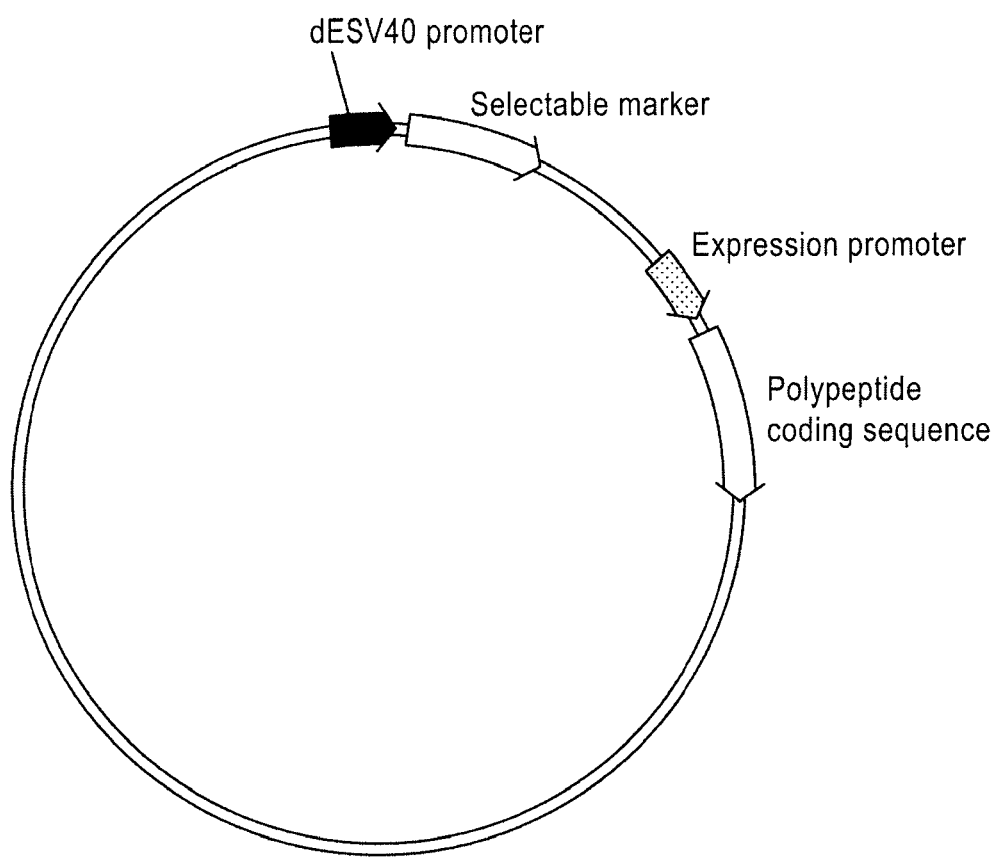

GCATGCATCTCAATTAGTCAGCAACCATAGTCCCGCCCCTAAC
TCCGCCCATCCCGCCCCTAACTCCGCCCAGTTCCGCCCATTCT
CCGCCCCATGGCTGACTAATTTTTTTATTTATGCAGAGGCCG
AGGCCGCCTCGGCCTCTGAGCTATTCCAGAAGTAGTGAGGAGG
CTTTTTTGGAGGCCTAGGCTTTTGCAAAAGCTT

FIG. 1

VECTORS AND HOST CELLS COMPRISING A MODIFIED SV40 PROMOTER FOR PROTEIN EXPRESSION

1. BACKGROUND

Recombinant proteins are used in a wide range of contexts, from bio-industrial applications where proteins are used in the manufacturing of a commercially useful product, such as a biofuel, to therapeutic applications where proteins are used to treat a disease or condition. The production of recombinant proteins is carried out in cells engineered to express such proteins at high levels and which are grown in large quantities, often in liquid culture. The process of developing a cell line that produces a recombinant protein in large quantities and is adapted to growth under conditions suitable for commercial scale production is lengthy. Often, initial development and screening of cell lines is performed in adherent culture until candidate high yield recombinant cell lines are identified and subsequently, further development is performed to optimize the candidate cell lines for large scale production in suspension culture. Additional time and effort is often required for recombinant proteins that are intended for therapeutic applications in humans, where safety considerations favor the development of cell lines adapted to grow in defined media, free of heterogeneous animal components. Thus, even after initial cell line development is complete, a further round of development and optimization is often required to generate a suitable recombinant cell line expressing high levels of the polypeptide of interest, that can be used for commercial production. This process is time consuming and inefficient as it requires multiple rounds of cell line development. There is a need for tools and streamlined processes that shorten the time it takes to develop a high yield recombinant cell line that is suitable for commercial production of proteins, especially therapeutic proteins.

2. SUMMARY

As disclosed in the present application, applicants have developed tools and a method for the streamlined generation of recombinant mammalian cell lines that are adapted to grow under conditions that resemble commercial production conditions. In particular, the present disclosure is based, in part, on applicants' discovery that expression vectors encoding a polypeptide of interest, such as a therapeutic protein, and a selectable marker where the selectable marker is operably linked to, or under the control of, an SV40 promoter that has been weakened by partial deletion of the enhancer region ("dESV40 promoter") can be used to generate recombinant cell lines capable of producing the polypeptide of interest in high yield in culture.

In a first aspect, the present disclosure provides vectors useful for developing recombinant mammalian cell lines that stably express high levels of a polypeptide of interest, such as a therapeutic protein (e.g., a therapeutic antibody). The vectors generally comprise a polynucleotide sequence encoding a selectable marker (selectable marker coding sequence) and an expression cassette comprising a polynucleotide sequence encoding a polypeptide of interest (polypeptide coding sequence). The expression cassette comprises polypeptide coding sequence operably linked to, or under the control of, a promoter capable of effecting expression in a mammalian cell line of interest ("expression promoter"), for example a mammalian cell line that will be used for large scale or commercial production of the encoded polypeptide. The selectable marker coding sequence is operably linked to, or under the control of, a selectable marker promoter. As provided herein, the selectable marker promoter useful for expression in mammalian host cells is a dESV40 promoter. A polynucleotide sequence encoding a dESV40 promoter is illustrated in FIG. 1. The vectors may also include promoters and encoding regions for expression of additional polypeptides of interest, additional selectable markers and/or additional elements or features useful for expressing the polypeptide(s) of interest in mammalian host cells, as are well-known in the art. Specific embodiments of vectors as disclosed herein that include optional polyadenylation signal sequences are illustrated in FIG. 2C and FIG. 2E.

Where the mammalian host cell is a CHO cell, the expression vector can comprise a selectable marker coding sequence operably linked to a different selectable marker promoter. In such embodiments, the selectable marker promoter may be an SV40 promoter weakened by mutation in the TA-rich region as described herein in Section 4.1.2.

The vectors described herein are not limited with respect to the types or origin of polypeptides they can be used to express, and indeed can be used to express virtually any polypeptide of interest. In particular, the vectors are useful for expressing therapeutic proteins of mammalian and/or human origin, such as for example immunomodulators, hormones, including growth hormones, blood proteins, enzymes, antigens for vaccines, and immunoglobulins, including therapeutic antibodies. Further polypeptides of interest are described below in Section 4.1.1.

Nor are the vectors limited with respect to the choice of the expression promoter. The only requirement is that the expression promoter be capable of effecting expression in the mammalian cell line that will be used to express the encoded polypeptide of interest. The expression promoter may be constitutively active or inducible, as is known in the art. In some embodiments, the expression promoter is stronger than the selectable marker promoter. A wide variety of promoters suitable expressing polypeptides are known in the art, and include by way of example and not limitation, the cytomegalovirus immediate early (CMV IE) promoter. Additional promoters are described below in Section 4.1.1. Any of these promoters may be used in the vector described herein. The specific promoter used will be suited to the mammalian cell line used to express the encoded polypeptide of interest.

The selectable marker confers upon cells transfected with a vector as described herein a trait or characteristic that can be used to select or identify transfected cells from non-transfected cells, as is well-known in the art. Traits commonly used for selection include, but are not limited to, resistance to a toxin, heavy metal, antibiotic or other agent, prototrophy in an auxotrophic host, the ability to grow in a medium lacking an essential nutrient, the ability to synthesize an essential metabolite, etc. A variety of selectable markers in the context of expression vectors that confer one or more of these traits are known in the art. Suitable selectable markers are described below in Section 4.1.2. In a specific embodiment of the vectors described herein the selectable marker encodes dihydrofolate reductase (DFIFR), which allows transfected cells to grow in media lacking hypoxanthine and thymidine and confers resistance to methotrexate, or xanthine-guanine phosphoribosyltransferase (XGPRT), an enzyme in the purine salvage pathway which confers resistance to mycophenolic acid to transfected cells.

In a specific embodiment, the vectors described herein are useful for expressing therapeutic antibodies. Such specific vectors generally comprise (i) an expression cassette comprising a polynucleotide sequence encoding the heavy chain of the therapeutic antibody of interest ("heavy chain coding sequence"), and a polynucleotide sequence encoding the light chain of the therapeutic antibody of interest ("light chain coding sequence") and (ii) a selectable marker coding sequence. The heavy chain and light chain coding sequences are each operably linked to, or under the control of, expression promoters, which can be the same or different, but are preferably the same. Alternatively, the heavy and light chain coding sequences can be separated by an internal ribosome entry site ("IRES") and operably linked to, or under the control of, a single expression promoter. The selectable marker coding sequence is operably linked to, or under the control of, a dESV40 promoter described herein. Exemplary embodiments of vectors useful for producing therapeutic polypeptides of interest are illustrated in FIGS. 2C and 2E. In a specific embodiment of vectors useful for expressing therapeutic antibodies, the antibody encoded for expression is other than elotuzumab.

The vectors described herein can be used to stably transfect mammalian cells that have been adapted to grow in culture, preferably in suspension culture, yielding strains of cells useful for producing the encoded polypeptide(s) in cell culture in high yield. Thus, in another aspect, the present disclosure provides recombinant mammalian cells capable of producing a polypeptide of interest in high yield in culture. In a specific embodiment, the recombinant mammalian cell can be a mammalian cell that has been adapted to grow in suspension culture and that has been transfected with a vector as described herein. Mammalian host cells that have been adapted to grow in suspension culture and that can be used to create the recombinant mammalian cells include, but are not limited to, Chinese Hamster Ovary (CHO) cells (e.g., CHO-S, DG44, and DXB-11), mouse myeloma cells (e.g., NS0 and SP2/0 cells), baby hamster kidney (BHK-21) cells, human PER.C6® cells and human embryonic kidney (HEK-293) cells.

Applicants have developed a rapid process for developing a recombinant mammalian cell line capable of high volumetric production, or yield, of a polypeptide of interest. Recombinant mammalian cells capable of producing a polypeptide of interest in high yield in culture could be obtained in the absence of gene amplification, shortening the time from transfection to identification of suitable recombinant mammalian cells. The process can be carried out in suspension culture, allowing for the isolation of mammalian cells suited to growth under conditions relevant for commercial production. Thus, the present disclosure further provides a method for producing a recombinant mammalian cell, preferably suspension-culture adapted, that is capable of producing a recombinant protein in high yield in culture. The method generally comprises transfecting a mammalian cell with a vector of the present disclosure and selecting a cell that is capable of producing high quantities of a polypeptide of interest. Where the polypeptide of interest is an immunoglobulin, e.g., an antibody, the method comprises transfecting a mammalian cell with a vector of the present disclosure and selecting a cell that is capable of producing at least 0.5 g/L of the polypeptide of interest in a 10-day fed-batch culture.

Also provided herein are methods of using the recombinant mammalian cells described herein to produce a polypeptide of interest. Generally, the methods comprise culturing a stably transfected recombinant mammalian cell under conditions that result in the expression of the polypeptide of interest. The methods can further include a step of recovering the polypeptide of interest from the culture medium or cell lysates. The method can comprise additional isolation or purification steps, as described below in Section 4.4.

In a further aspect, the present disclosure provides a vector comprising a dESV40 promoter operably linked to a polypeptide coding sequence. In a specific embodiment, the dESV40 promoter corresponds to SEQ ID NO:1, shown in FIG. 1.

3. BRIEF DESCRIPTION OF THE FIGURES

Figure 2B:
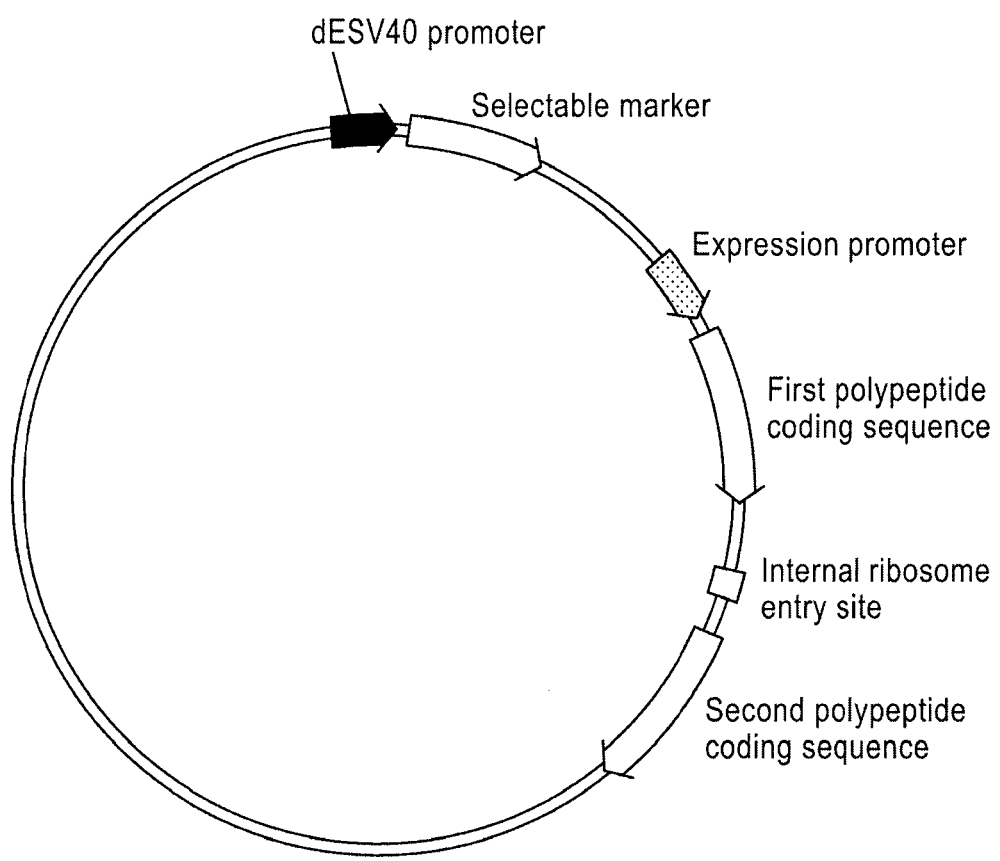
Figure 2C:
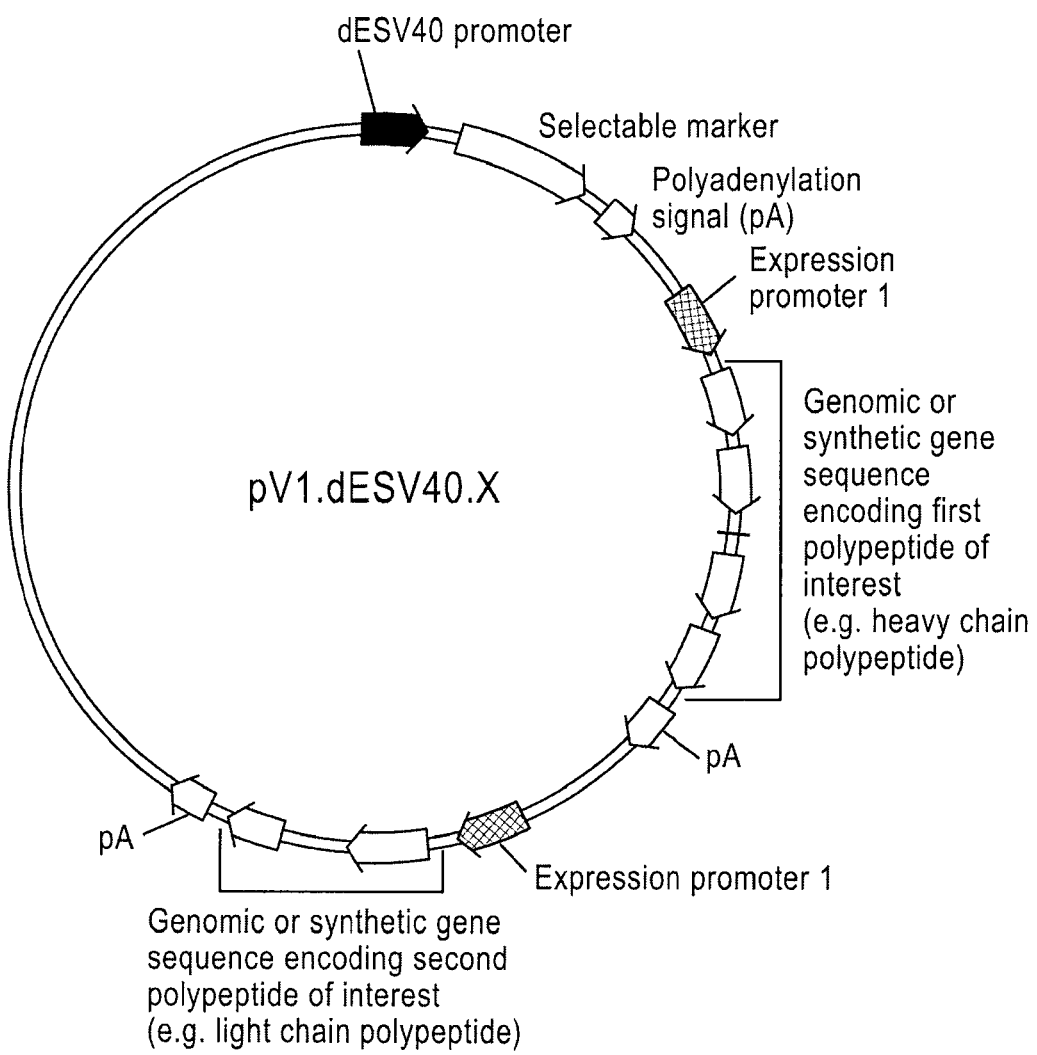
Figure 2D:
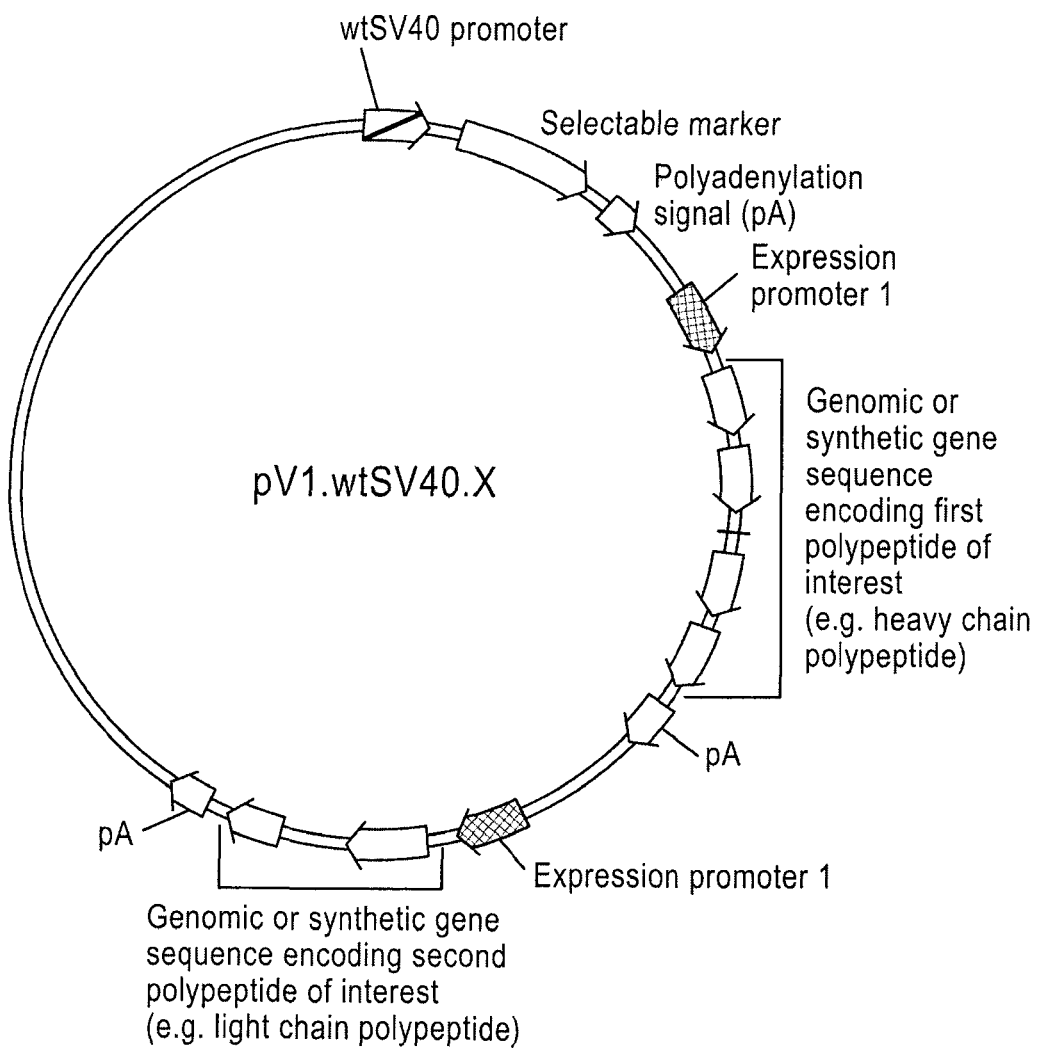
Figure 2E:
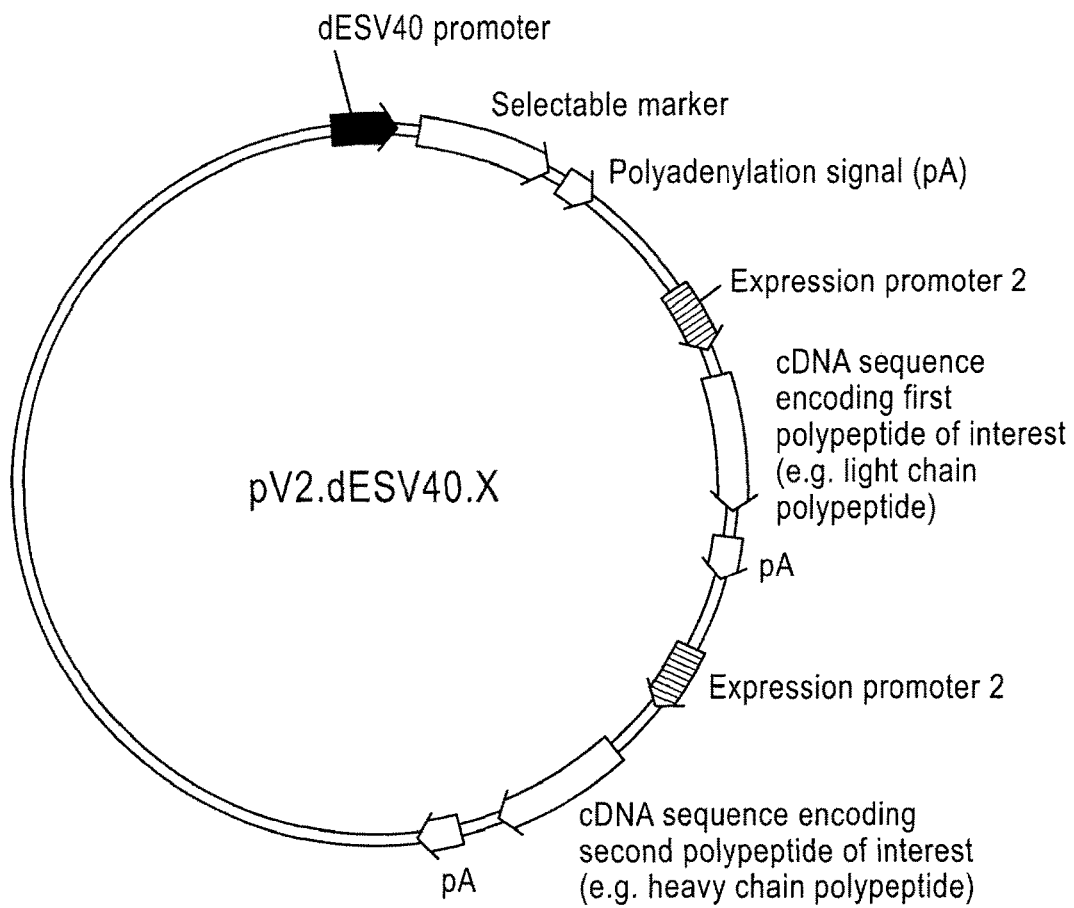
Figure 2F:
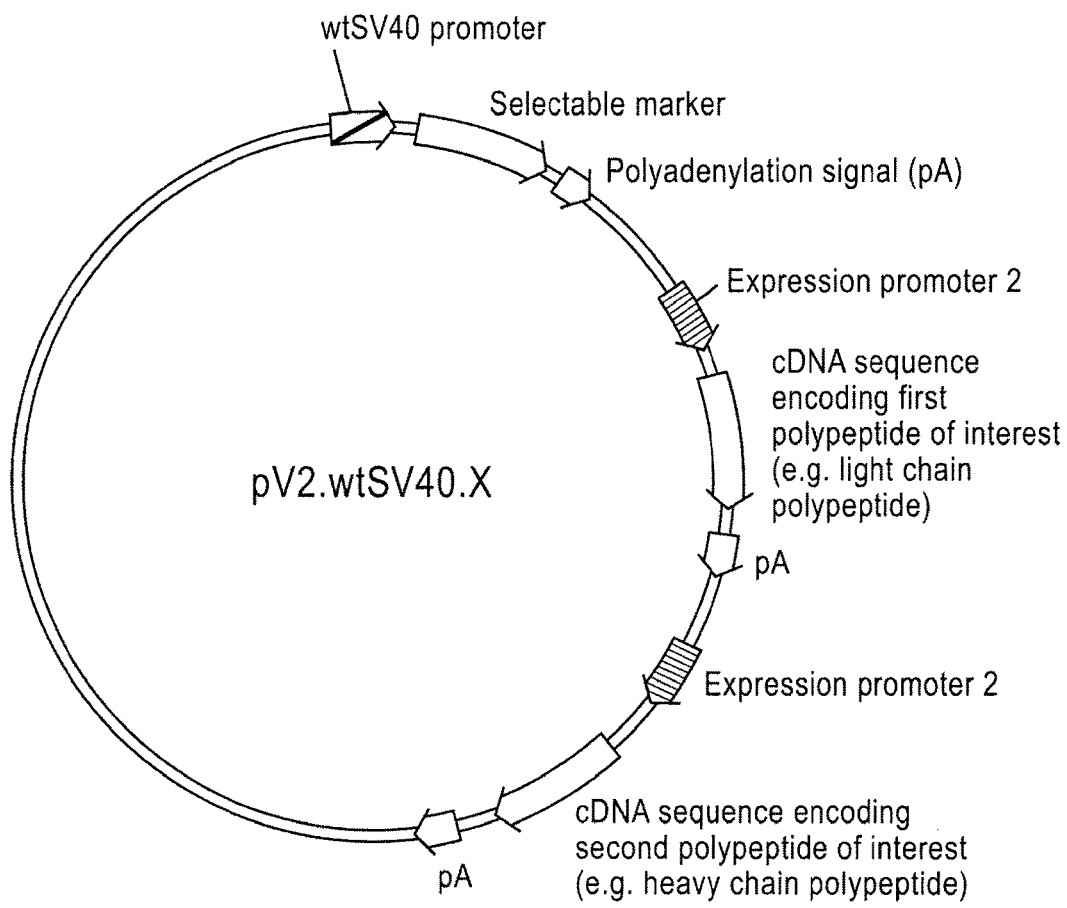
Figure 3:
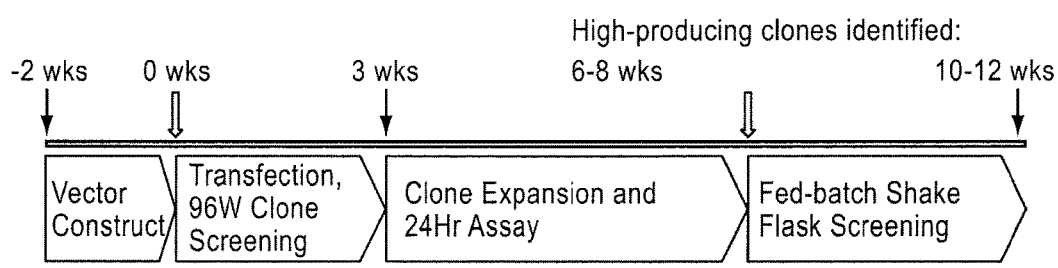
Figure 4A:
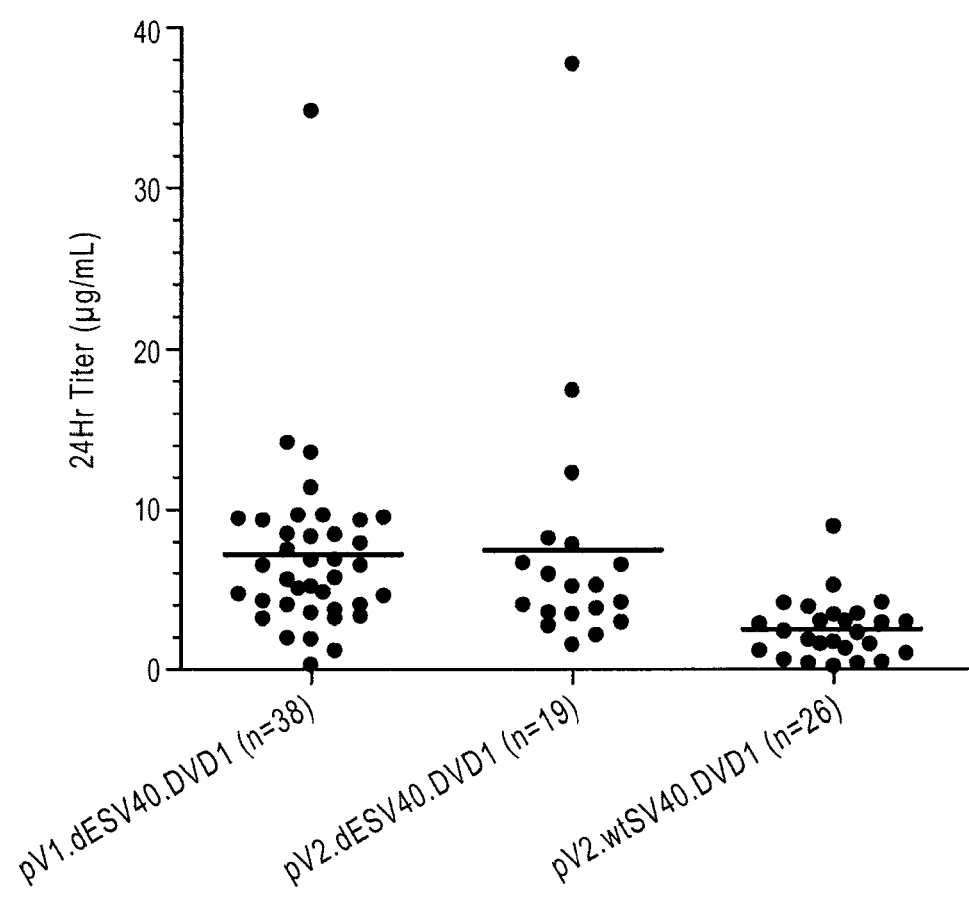
Figure 4B:
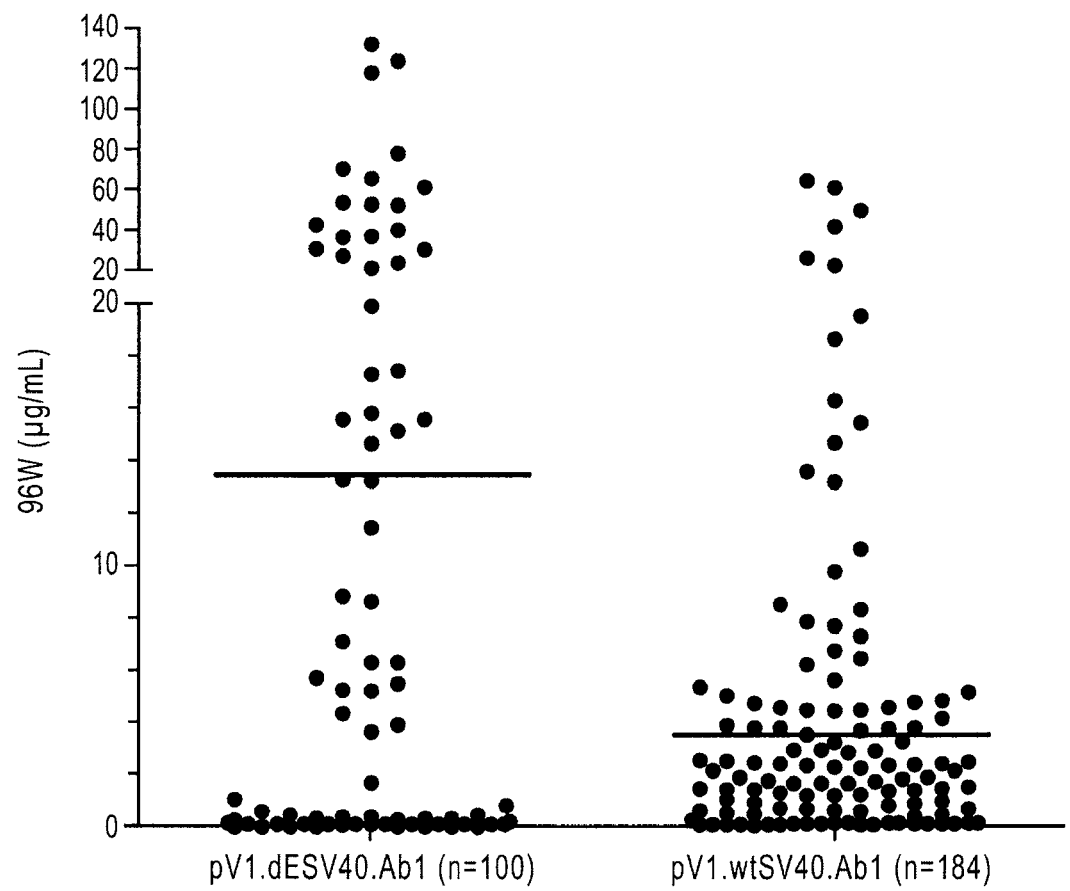
Figure 5A:
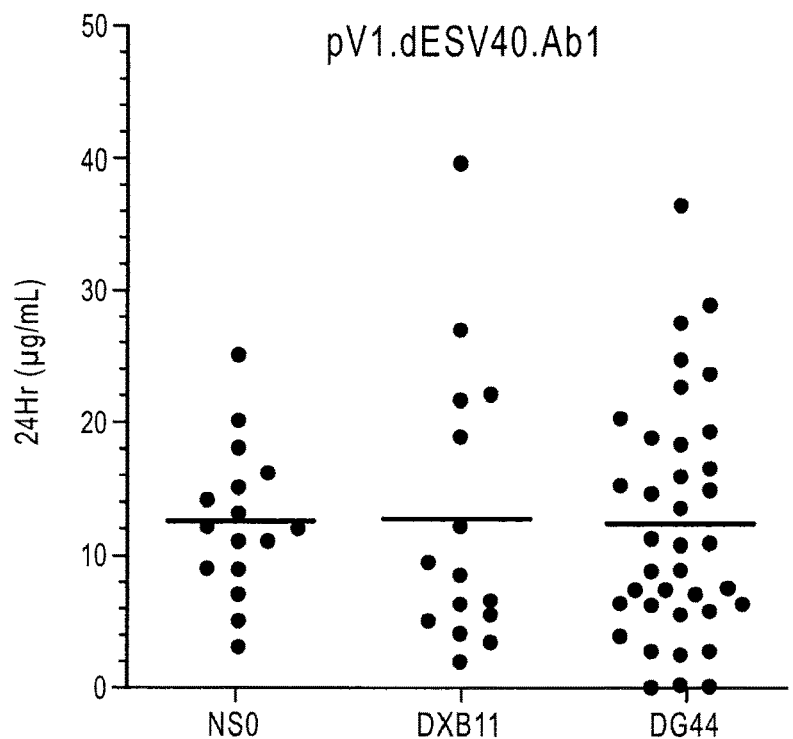
Figure 5B:
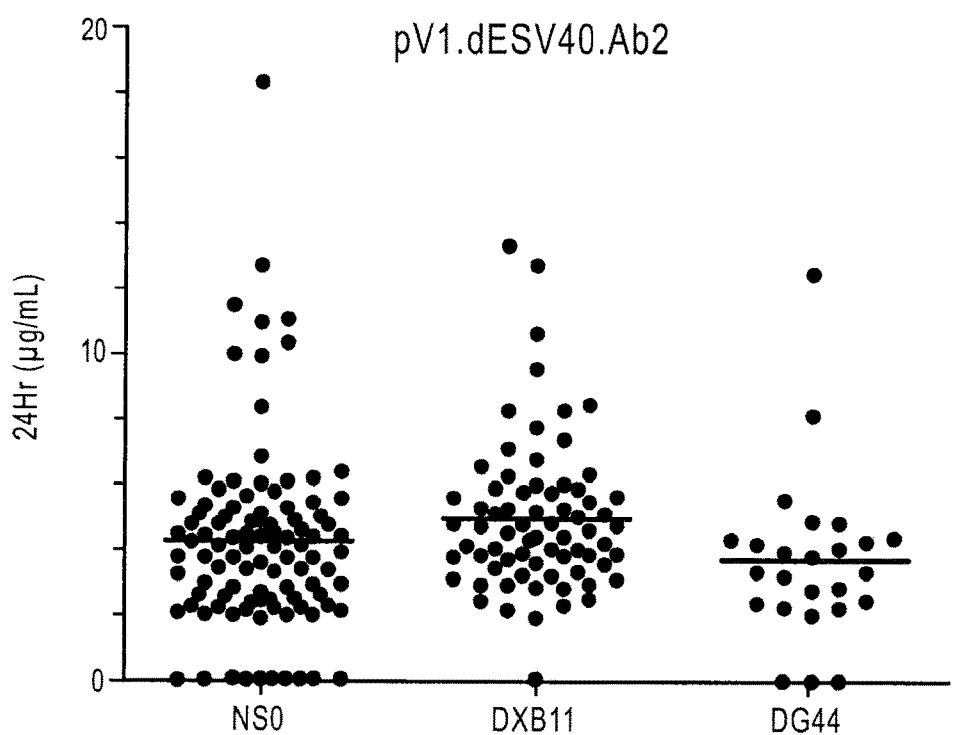
Figure 6:
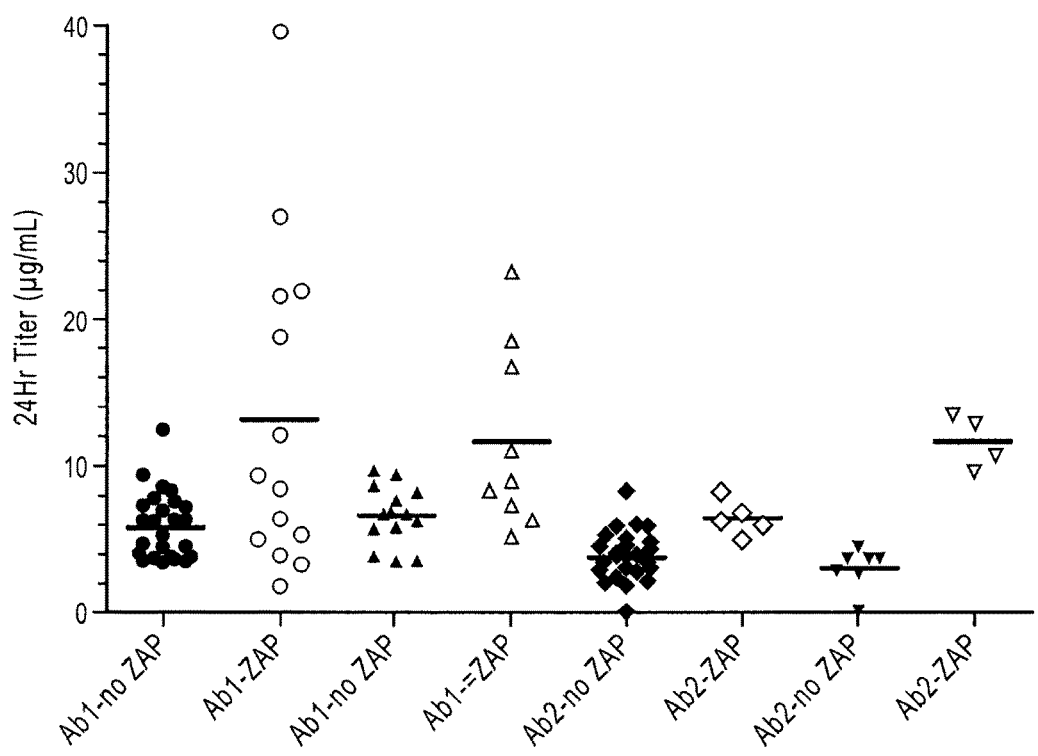

FIG. 1 provides the nucleotide sequence of an embodiment of a dESV40 promoter as described herein;

FIGS. 2A-F provide schematic illustrations of expression vectors comprising an expression cassette for effecting expression of one or more polypeptide(s) of interest and a selectable marker operably linked to a dESV40 or a wild type SV40 ("wtSV40") promoter;

FIG. 2A is a schematic illustration of an exemplary expression vector of the present disclosure, which comprises an expression cassette comprising a first polypeptide coding sequence operably linked to an expression promoter, and a selectable marker coding sequence operably linked to a dESV40 promoter;

FIG. 2B provides a schematic illustration of an exemplary expression vector of the present disclosure, which comprises an expression cassette comprising first and second polypeptide coding sequences operably linked to a single expression promoter, an internal ribosome entry site in between the first and second polypeptide coding sequences, and a selectable marker coding sequence operably linked to a dESV40 promoter;

FIG. 2C provides a schematic illustration of an exemplary expression vector of the present disclosure for expressing protein X, pV1.dESV40.X, which comprises an expression cassette comprising first and second polypeptide coding sequences, which are genomic or synthetic gene sequences, each operably linked to an expression promoter (expression promoter 1), a selectable marker coding sequence operably linked to a dESV40 promoter, and a polyadenylation signal (pA) at the 3' end of the selectable marker coding sequence and the first and second polypeptide coding sequences;

FIG. 2D provides a schematic illustration of a control vector for expressing protein X, pV1.wtSV40.X, which comprises an expression cassette comprising first and second polypeptide coding sequences, which are genomic or synthetic gene sequences, each operably linked to an expression promoter (expression promoter 1), a selectable marker coding sequence operably linked to a wtSV40 promoter, and a polyadenylation signal (pA) at the 3' end of the selectable marker coding sequence and the first and second polypeptide coding sequences;

FIG. 2E provides a schematic illustration of an exemplary expression vector of the present disclosure for expressing protein X, pV2.dESV40.X, which comprises an expression cassette comprising a first and second first and second polypeptide coding sequences, which are cDNA sequences, each operably linked to an expression promoter (expression promoter 2), a selectable marker coding sequence operably linked to a dESV40 promoter, and a polyadenylation signal (pA) at the 3' end of the selectable marker coding sequence and the first and second polypeptide coding sequences;

FIG. 2F provides a schematic illustration of a control vector for expressing protein X, pV2.wtSV40.X, which comprises an expression cassette comprising first and second polypeptide coding sequences, which are cDNA sequences, each operably linked to an expression promoter (expression promoter 2), a selectable marker coding sequence operably linked to a wtSV40 promoter, and a polyadenylation signal (pA) at the 3' end of the selectable marker coding sequence and the first and second polypeptide coding sequences;

FIG. 3 provides a flow diagram of a process for identifying high yield recombinant mammalian cells;

FIGS. 4A-B provide a graph of protein yield (μg/mL) from recombinant mammalian cells transfected with vectors bearing either a dESV40 promoter or wtSV40 promoter. FIG. 4A shows protein yield for test protein DVD1 expressed in vectors pV1.dESV40.DVD1, pV2.dESV40.DVD1, or pV2.wtSV40.DVD1. FIG. 4B shows protein yield for test protein Ab1 expressed in vectors pV1.dESV40.Ab1 or pV1.wtSV40.Ab1;

FIGS. 5A-B provide graphs of protein yield (μg/mL) from recombinant mammalian cells generated by transfecting three different mammalian cell lines with expression vector pV1.dESV40.Ab1 (FIG. 5A) or pV1.dESV40.Ab2 (FIG. 5B); and FIG. 6 provides a graph of protein yield (μg/mL) from recombinant mammalian cells transfected with pV1.dESV40.Ab1 or pV1.dESV40.Ab2, selected in animal-component free medium with or without ZAP-CHO® supplementation ("no ZAP" versus "ZAP").

4. DETAILED DESCRIPTION

As shown in the Example below, Applicants have discovered that expression vectors that bear a selectable marker operably linked to, or under the control of, a simian virus early (SV40) promoter that has been weakened by partial deletion of the enhancer region, the nucleotide sequence of which is shown in FIG. 1, in addition to an expression cassette including a polypeptide coding sequence for a polypeptide of interest under the control of a promoter operable in a mammalian cell, can be used to generate recombinant cell lines having high yield of the polypeptide of interest. Without being bound by theory, it is believed that selectable markers under the control of SV40 promoters in which enhancer elements have been partially deleted ("dESV40") facilitates the identification of stably transfected mammalian cells in which the expression vector is integrated into a chromosomal region that is transcriptionally active, yielding high expression levels of the polypeptide of interest in the absence of gene amplification. By using mammalian cell lines that are already adapted to growth in suspension culture as host cells, applicants have further developed a shortened process for the generation of recombinant mammalian cells capable of producing high levels of a polypeptide of interest. Accordingly, the present disclosure provides expression vectors, recombinant mammalian cells capable of producing high levels of a polypeptide of interest, and methods of producing and using such recombinant mammalian cells.

4.1. Expression Vectors

The expression vectors of the present disclosure comprise an expression cassette and a polynucleotide sequence encoding a selectable marker (selectable marker coding sequence), under the control of an SV40 promoter that has been weakened by partial deletion of the enhancer region. Each of these components is described in further detail below.

4.1.1. Expression Cassettes

Expression cassettes comprise a polynucleotide sequence encoding a polypeptide of interest (polypeptide coding sequence) operably linked, or under the control of, a promoter capable of effecting expression in a mammalian cell line of interest ("expression promoter"). Expression cassettes can comprise one or more polypeptide coding sequence(s). Accordingly, expression cassettes comprise at least a first, and optionally a second, third, fourth, etc., polypeptide coding sequence. Thus, in some embodiments, expression cassettes comprise a first and second polypeptide coding sequences, which can be under the control of a single promoter or separate promoters.

Where the first polypeptide coding sequence is operably linked to, or under the control of, a first expression promoter and the second polypeptide sequence is under the control of a second expression promoter, the first and second expression promoters can be the same or different. Where two or more polypeptide coding sequences are under the control of a single expression promoter, as depicted in FIG. 2B, an internal ribosome binding site ("IRES") is preferably included in between each polypeptide coding sequence.

The polypeptide coding sequence can be from a eukaryote or a prokaryote, and can be a genomic sequence, a synthetic gene, or a cDNA sequence. Where the polypeptide coding sequence is from a eukaryotic gene, it can, but need not, include introns which can be spliced out during transcriptional processing in the mammalian cell.

The polypeptide coding sequence can be a fusion of two or more coding sequences and contain multiple functional domains in a single polypeptide, referred to as a fusion protein. A fusion protein can incorporate sequences designed to ensure proper processing or targeting of the polypeptide within the host cell, e.g., a signal sequence as will be discussed further below. Fusion proteins can also contain sequences that facilitate detection or purification of the polypeptide of interest, such as a sequence encoding an epitope tag that is recognized by an anti-tag antibody. The coding sequence for the epitope tag is generally placed at one terminus (carboxy or amino) of the coding sequence for the polypeptide of interest. Various tag polypeptides and their respective antibodies are available. Examples include poly-histidine (poly-his) or poly-histidine-glycine (poly-his-gly) tags; HIS6 and metal chelation tags, the flu HA tag polypeptide and its antibody 12CA5 (Field, et al. (1988) Mol. Cell. Biol. 8:2159-2165); the c-myc tag and the 8F9, 3C7, 6E10, G4, B7, and 9E10 antibodies thereto (Evan, et al. (1985) Molecular and Cellular Biology 5:3610-3616); and the Herpes Simplex virus glycoprotein D (gD) tag and its antibody (Paborsky, et al. (1990) Protein Engineering 3(6): 547-553). Other tag polypeptides include the Flag-peptide (Hopp, et al. (1988) BioTechnology 6:1204-1210); the KT3 epitope peptide (Martin, et al. (1992) Science 255:192-194); tubulin epitope peptide (Skinner, et al. (1991) J. Biol. Chem. 266:15163-15166); and the T7 gene 10 protein peptide tag (Lutz-Freyermuth, et al. (1990) Proc. Natl. Acad. Sci. USA 87:6393-6397).

The expression vectors of the present disclosure can be used to express virtually any polypeptide of interest. In particular, vectors are useful for expressing therapeutic proteins (i.e., a polypeptide having a therapeutic biological activity) of mammalian, e.g., human origin.

The polypeptide of interest can be a polypeptide used to generate conjugates with novel properties by coupling with other molecules, such as, without limitation, a drug, a toxin (e.g., an immunotoxin), a radionuclide, or a tracer molecule. In a specific example, the polypeptide of interest is an immunoglobulin that can be coupled to a drug to generate an antibody-drug conjugate.

Examples of suitable therapeutic proteins include: erythropoietin, cytokines such as interferon-α, interferon-β, interferon-γ, interferon-o, and granulocyte-CSF, GM-CSF, coagulation factors such as factor VIII, factor IX, and human protein C, antithrombin III, thrombin, soluble IgE receptor α-chain, IgG, IgG fragments, IgG fusions, IgM, IgA, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon like protein 1 and IL-2 receptor agonist.

The polypeptide of interest can be an immunoglobulin, including, but not limited to, an antibody (e.g., monoclonal, chimeric, humanized, or fully human), an antibody fragment (e.g., Fv, single chain Fv, Fab, Fab', F(ab')2), immunoglobulin fusion protein (e.g., Fe-fusion protein, antibody-enzyme fusion protein, antibody-immunotoxin fusion protein), a bi-specific antibody, and a dual variable domain immunoglobulin. Dual variable domain immunoglobulins (DVD Igs) are synthetic immunoglobulins comprising two or more antigen binding domains that can be designed to recognize multiple antigens. See, e.g., U.S. App. Pub. no. 2011/0008766, describing DVD Igs, and Wu et al., 2007, Nature Biotechnology 25:1290-1297, the contents of which are incorporated herein by reference. Immunoglobulin molecules can be of any type (e.g., IgG, IgE, IgM, IgD, IgA IgY), class (e.g., IgG1, IgG2, IgG3, IgG4, IgA1) or subclass.

The immunoglobulin can be a fusion protein, combining constant regions and variable regions from different genes into a single polypeptide coding sequence or fusing an antibody with an entirely different molecule that confers new properties, e.g., an enzyme. In some embodiments, the polypeptide coding sequence includes two or more amino acid residues that are used to link sequences encoding different regions of an antibody heavy or light chain. Such linker polypeptide sequences are well known in the art (see, e.g., Holliger et al., 1993, Proc. Natl. Acad. Sci. USA 90:6444-6448; Poljak et al., 1994, Structure 2:1121-1123).

Therapeutic antibodies are of particular interest. In a specific embodiment, the expression cassette comprises a polynucleotide sequence encoding the heavy chain of the therapeutic antibody of interest ("heavy chain coding sequence") and a polynucleotide sequence encoding the light chain of the therapeutic antibody of interest ("light chain coding sequence"). The heavy chain and light chain coding sequences are each operably linked to, or under the control of, expression promoters, which can be the same or different, but are preferably the same. Alternatively, the heavy and light chain coding sequences can be separated by an IRES and operably linked to, or under the control of, a single expression promoter. In a specific embodiment of vectors useful for expressing therapeutic antibodies, the vector comprises an expression cassette which comprises polynucleotide sequences encoding an antibody other than elotuzumab. In a further specific embodiment, the therapeutic antibody is other than an antibody having a heavy chain variable region corresponding to SEQ ID NO:5 and a light chain variable region corresponding SEQ ID NO:6, of U.S. Pat. No. 7,842,293.

For some applications, it may be desirable for the polypeptide of interest to be secreted by the mammalian cell. For such application, the polypeptide coding sequence can include, or be engineered to include, a signal sequence encoding a leader peptide that directs the polypeptide of interest to the mammalian cell's secretory pathway. The signal sequence, when present, is in an appropriate translation reading frame with the mature polypeptide coding sequence. Accordingly, the polypeptide coding sequence can further encode a signal sequence operably linked to the N-terminus of the polypeptide of interest, where the signal sequence contains a sequence of amino acids that directs the polypeptide of interest to the secretory system of the recombinant mammalian cell, resulting in secretion of the mature polypeptide of interest from the recombinant mammalian cell into the medium in which the recombinant mammalian cell is growing. The signal sequence is entirely or partially cleaved from the fusion protein prior to secretion of the mature polypeptide of interest. The signal sequence employed can be endogenous or non-endogenous to the polypeptide of interest and/or the recombinant mammalian cell. Preferably, the signal sequence is a signal sequence that facilitates protein secretion from a mammalian cell. In certain embodiments, therefore, the polypeptide coding sequence includes a sequence encoding a signal sequence, yielding a polypeptide of interest in the form of a polypeptide comprising an N-terminal signal sequence for secretion of the protein from the recombinant mammalian cell.

Expression promoters of the present disclosure can be any promoter capable of effecting expression in the mammalian cell line that is used. A variety of promoters is known in the art, including mammalian viral promoters and promoters of mammalian genes.

Mammalian viral genes are often highly expressed and have a broad host range, therefore sequences encoding mammalian viral genes provide particularly useful promoter sequences. Specific examples of mammalian viral promoters include the Rous sarcoma virus (RSV) promoter (see, e.g., Yamamoto et al., 1980, Cell 22:787-797), the cytomegalovirus immediate early gene (CMV IE) promoter (Boshart et al., 1985, Cell 41(2):521-30) and cytomegalovirus major intermediate-early (CMV MIE) promoter (Akrigg, et al., 1985, Virus Res. 2:107-121), the SV40 early (SV40) promoter (Benoist and Chambon, 1981, Nature 290:304-310), the Adenovirus major late promoter (AML) (Tooze, 1980, Molecular Biology of Tumor Viruses, Part II: DNA Tumor Viruses, Cold Spring Harbor Laboratory, Cold Spring Harbor, N.Y.), the mouse mammary tumor virus LTR promoter, and the Herpes thymidine kinase gene promoter (see, e.g., Wagner et a, 1981, Proc. Natl. Acad. Sci. U.S.A. 78:1441-1445). In addition, sequences derived from non-viral genes, such as the human β-actin promoter (ACTB) gene, the elongation factor-1α (EF1α) gene, the phosphoglycerate kinase (PGK) gene, the ubiquitinC (UbC) gene, and the murine metallotheionin gene, also provide useful promoter sequences.

In some embodiments, expression promoters of the present disclosure are promoters that are stronger than the selectable marker promoter, i.e., promoters that provide a higher level of expression than the dESV40 promoter described herein, e.g., at least 1.5 or more times, at least 2 or more times, at least 2.5 or more times, at least 3 or more times the activity of the dESV40 promoter. Expression promoter activity can be measured by comparing the yield of a reporter protein, e.g., green fluorescent protein, in a mammalian host cell transfected with a vector containing the test expression promoter operably linked to a reporter protein coding sequence relative to a mammalian host cell transfected with a reference vector in which the test promoter sequence is substituted with the dESV40 promoter shown in FIG. 1, grown in suitable medium.

Expression promoters may also be operably linked to one or more enhancer elements (enhancer). The presence of an enhancer will usually increase expression levels. An enhancer is a regulatory DNA sequence that can stimulate transcription up to 1000-fold when linked to homologous or heterologous promoters, with synthesis beginning at the normal RNA start site. Enhancers derived from viruses may be particularly useful, because they usually have a broader host range. Examples include the SV40 early gene enhancer (Dijkema et al., 1985, EMBO J. 4:761) and the enhancer/promoters derived from the long terminal repeat (LTR) of the Rous Sarcoma Virus (Gorman et al., 1982, Proc. Natl. Acad. Sci. 79:6777) and from human cytomegalovirus (Boshart et al., 1985, Cell 41:521). Additionally, some enhancers are regulatable and become active only in the presence of an inducer, such as a hormone or metal ion (Sassone-Corsi and Borelli, 1986, Trends Genet. 2:215; Maniatis et al., 1987, Science 236:1237).

4.1.2. Selectable Markers

Expression vectors further comprise a polynucleotide sequence encoding a selectable marker operably linked to, or under the control of, a selectable marker promoter. As provided herein, the selectable marker promoter useful in transfecting mammalian host cells is an SV40 promoter that has been weakened by partial deletion of two 72-nucleotide repeats (or 72-nucleotide tandem repeat) that form an enhancer element in the wild type SV40 promoter, referred to herein as a dESV40 promoter. The deletion of about four-fifths of the 72-nucleotide tandem repeat results in a promoter that retains the ability to drive expression but at a reduced level as compared to the wild type SV40 promoter. The nucleotide sequence of an exemplary dESV40 promoter is shown in FIG. 1. It is expected that dESV40 promoter sequences having at least a 25 nucleotide fragment of the 72-nucleotide tandem repeat but less than a single 72-nucleotide repeat will be useful to effect expression of the selectable marker in the vectors of the present disclosure. In some embodiments, the dESV40 promoter is a promoter comprising a nucleotide sequence having at least 95%, at least 96%, at least 97%, at least 98%, or at least 99% identity to SEQ ID NO:1.

Where the mammalian host cell is a CHO cell, as described below in Section 4.2, the selectable marker promoter, alternatively, can be an SV40 promoter weakened by mutation in the TA rich region, e.g., A-series mutations as described in Pauly et al., 1992, Nucl. Acids Res. 20:975-982, incorporated by reference herein.

Skilled artisans would appreciate that the dESV40 promoter described herein can be used generally to drive expression of a polypeptide coding sequence. Accordingly, the present disclosure further provides a vector comprising a dESV40 promoter operably linked to a polypeptide coding sequence. In an exemplary embodiment, the dESV40 promoter corresponds in sequence to SEQ ID NO:1.

The selectable marker promoter is operably linked to a selectable marker coding sequence, which confers upon cells transfected with an expression vector as described herein a trait or characteristic that be used to identify transfected cells from non-transfected cells. Selectable markers are well known in the art. They can confer traits such as, but not limited to, resistance to a toxin, heavy metal, antibiotic, or other agent, prototrophy in an auxotrophic host, the ability to grow in a medium free of an essential nutrient, the ability to synthesize an essential metabolite. Selectable markers commonly used in transfecting mammalian cells include mammalian genes such as dihydrofolate reductase (DHFR) and bacterial genes, such as E. coli xanthine-guanine phosphoribosyltransferase (gpt). Examples of selectable markers which confer antibiotic resistance include neomycin, puromycin, hygromycin and phleomycin. Further exemplary selectable markers include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), pyr4 (orotidine-5'-monophosphate decarboxylase) and trpC (anthranilate synthase). See also, U.S. Pat. No. 5,627,033, incorporated herein by reference.

4.1.3. Suitable Vectors and Methods of Making Expression Vectors

The expression cassette, selectable marker and selectable marker promoter described above are provided in expression vectors. The choice of the vector will depend on several factors, including the compatibility of the vector with the mammalian cell into which the vector is to be introduced (e.g., a mammalian cell, or a host cell such as a bacterial cell, useful for propagating or amplifying the vector), and the ability of the vector to integrate into the mammalian cell genome. The vector can be a viral vector, a phage, a phagemid, a cosmid, a fosmid, a bacteriophage, an artificial chromosome, a cloning vector, a shuttle vector, a plasmid (linear or closed circular), or the like. Vectors can include chromosomal, non-chromosomal and synthetic DNA sequences. Large numbers of suitable vectors are known to those of skill in the art, and are commercially available. Examples of suitable vectors are provided in Sambrook et al., eds., Molecular Cloning: A Laboratory Manual (2nd Ed.), Vols. 1-3, Cold Spring Harbor Laboratory (1989), and Ausubel et al., eds., Current Protocols in Molecular Biology, John Wiley & Sons, Inc., New York (1997). Particularly useful vectors include vectors obtained from commercial sources, such as Invitrogen and Promega.

The relative orientation of the polypeptide coding sequence(s) and the selectable marker coding sequence is not important. The one or more polypeptide coding sequence(s) and selectable marker coding sequence can be in the same or in different orientations.

Expression vectors may include additional features or elements useful for expressing the polypeptide(s) of interest in mammalian host cells as are well-known in the art. Such features include enhancer elements, transcription initiation sequences and ribosome binding sites, polyadenylation signal sequences, termination sequences and other features important for nuclear export, translation, and/or stability of the mRNA.

Vectors described herein typically also contain features useful for cloning and propagation in a prokaryotic, e.g. bacterial, cell, such as an origin of replication enabling autonomous replication and a selectable marker for screening of positive clones.

Techniques for the manipulation of nucleic acids, including techniques for the synthesis, isolation, cloning, detection, and identification are well known in the art and are well described in the scientific and patent literature. See, e.g., Sambrook et al., eds., Molecular Cloning: A Laboratory Manual (2nd Ed.), Vols. 1-3, Cold Spring Harbor Laboratory (1989); Ausubel et al., eds., Current Protocols in Molecular Biology, John Wiley & Sons, Inc., New York (1997); Tijssen, ed., Laboratory Techniques in Biochemistry and Molecular Biology: Hybridization With Nucleic Acid Probes, Part I. Theory and Nucleic Acid Preparation, Elsevier, N.Y. (1993). Nucleic acids comprising the expression vectors described herein or components thereof include isolated, synthetic, and recombinant nucleic acids.

Expression vectors and components thereof can readily be made and manipulated from a variety of sources, either by cloning from genomic or complementary DNA, e.g., by using the well known polymerase chain reaction (PCR). See, for example, Innis et al., 1990, PCR Protocols: A Guide to Methods and Application, Academic Press, New York. Expression cassettes and components thereof can also be made by chemical synthesis, as described in, e.g., Adams, 1983, J. Am. Chem. Soc. 105:661; Belousov, 1997, Nucleic Acids Res. 25:3440-3444; Frenkel, 1995, Free Radic. Biol. Med. 19:373-380; Blommers, 1994, Biochemistry 33:7886-7896; Narang, 1979, Meth. Enzymol. 68:90; Brown, 1979, Meth. Enzymol. 68:109; Beaucage, 1981, Tetra. Lett. 22:1859; U.S. Pat. No. 4,458,066. The procedures used to ligate the components described herein to construct the recombinant expression vectors are well known to one skilled in the art (see, e.g., Sambrook et al., eds., Molecular Cloning: A Laboratory Manual (2nd Ed.), Vols. 1-3, Cold Spring Harbor Laboratory (1989)).

4.2. Recombinant Mammalian Cells

Expression vectors of the present disclosure are transfected into mammalian cells which are adapted to grow in culture to produce recombinant mammalian cells, which are capable of producing a polypeptide of interest in high yield in culture.

High yield, or high volumetric productivity, as used herein refers to the ability of cells to produce high levels of a polypeptide of interest. The particular yield will depend on the polypeptide of interest and can be at least 0.05 g/L, at least 0.1 g/L, at least 0.15 g/L, at least 0.2 g/L, at least 0.25 g/L, at least 0.3 g/L, at least 0.35 g/L, at least 0.4 g/L, at least 0.45 g/L, at least 0.5 g/L, at least 0.6 g/L, at least 0.7 g/L, at least 0.8 g/L, at least 0.9 g/L, at least 1 g/L, at least 1.5 g/L, at least 2 g/L, or more, in a 10-day culture grown in fed batch conditions, using a feed medium suitable for the mammalian host cell and containing amino acids, vitamins, or trace elements. In specific embodiments, recombinant mammalian cells of the present disclosure express an immunoglobulin and are capable of producing at least 0.5 g/L, at least 0.6 g/L, at least 0.7 g/L, at least 0.8 g/L, at least 0.9 g/L, at least 1 g/L, at least 1.5 g/L, at least 2 g/L, or more, preferably up to about 3 g/L, 4 g/L, 5 g/L or 10 g/L when grown under the culture conditions described above.

Yield can also be measured in terms of the specific productivity of a cell line, determined based on the amount of polypeptide produced per cell per day (expressed as pg/cell/day). Recombinant mammalian cells of the present disclosure are capable of producing at least 1 pg/cell/day, at least 2 pg/cell/day, at least 3 pg/cell/day, at least 4 pg/cell/day, at least 5 pg/cell/day, at least 6 pg/cell/day, at least 7 pg/cell/day, at least 8 pg/cell/day, at least 9 pg/cell/day, at least 10 pg/cell/day, at least 11 pg/cell/day, at least 12 pg/cell/day, at least 13 pg/cell/day, at least 14 pg/cell/day, at least 15 pg/cell/day, at least 20 pg/cell/day, at least 25 pg/cell/day, or more, preferably up to 50 pg/cell/day in a 10-day culture grown in fed batch conditions, using a feed medium suitable for the mammalian host cell and containing amino acids, vitamins, or trace elements. In specific embodiments, recombinant mammalian cells of the present disclosure express an immunoglobulin and have a specific productivity of at least 10 pg/cell/day, at least 11 pg/cell/day, at least 12 pg/cell/day, at least 13 pg/cell/day, at least 14 pg/cell/day, at least 15 pg/cell/day, at least 20 pg/cell/day, at least 25 pg/cell/day, or more, preferably up to 50 pg/cell/day under the culture conditions described above.

Large-scale production of proteins for commercial applications is typically carried out in suspension culture. Therefore, mammalian host cells used to generate the recombinant mammalian cells described herein can, but need not be, adapted to growth in suspension culture. A variety of host cells adapted to growth in suspension culture are known, including mouse myeloma NS0 cells and CHO cells from CHO-S, DG44, and DXB11 cell lines. Other suitable cell lines include mouse myeloma SP2/0 cells, baby hamster kidney BHK-21 cells, human PER.C6® cells, human embryonic kidney HEK-293 cells, and cell lines derived or engineered from any of the cell lines disclosed herein.

The recombinant mammalian cells are preferably stably transfected, where the expression cassette and selectable marker are integrated into the mammalian host cell genome.

4.3. Methods of Obtaining High Yield Recombinant Mammalian Cells

Applicants have developed a process for obtaining a recombinant mammalian cell capable of producing a polypeptide of interest in high yield in culture. Generally, the method comprises transfecting a mammalian cell with an expression vector of the present disclosure and selecting a cell capable of producing a polypeptide of interest in high yield in culture.

An exemplary process with which recombinant mammalian cells of the present disclosure can be obtained in six to eight weeks is described in the Example below and depicted schematically in FIG. 3. The method does not require gene amplification in order to generate recombinant mammalian cells with a high volumetric productivity of a polypeptide of interest.

Techniques for transfecting mammalian cells with expression vectors are known in the art. Recombinant mammalian cells as provided herein are generated by introducing an expression vector of the present disclosure into a suitable mammalian cell. Numerous techniques for introducing nucleic acids into mammalian cells are known. Nucleic acids may be introduced into the cells using any of a variety of techniques, including transformation, transfection, transduction, or viral infection. Particular methods include calcium phosphate transfection, DEAE-Dextran mediated transfection, lipofection, or electroporation (Davis, L., Dibner, M., Battey, I., Basic Methods in Molecular Biology, (1986)). General transformation techniques are known in the art (See, e.g., Ausubel et al., eds., Current Protocols in Molecular Biology, John Wiley & Sons, Inc., New York (1997); and Sambrook et al., eds., Molecular Cloning: A Laboratory Manual (2nd Ed.), Vols. 1-3, Cold Spring Harbor Laboratory (1989), and Campbell et al., 1989, Curr. Genet. 16:53-56).

Selection of stably transfected recombinant cells is carried out by growing cells in selection medium, whereby only transfected cells are able to grow. Media and growth conditions for selecting transfected recombinant cells are well known in the art. Generally, the choice of medium is based on the selectable marker used, where the medium lacks a component necessary for cell growth, as in the case of a selectable marker that confers prototrophy or the ability to make an essential metabolite, or contain a component that is toxic to untransformed cells, as in the case of a selectable marker that confers resistance to a biocide, antibiotic, or heavy metal. In an exemplary embodiment, the selectable marker is DHFR and cells are grown in medium lacking hypoxanthine and thymidine and containing methotrexate. In another exemplary embodiment, the selectable marker is E. coli gpt and cells are grown in medium containing mycophenolic acid and xanthine.

As shown in the Example below, applicants have observed that it is possible to select for stably transfected high yield recombinant mammalian cells by growing cells in medium that lacks animal-derived components, such as serum proteins, but is supplemented with recombinant proteins. Accordingly, the methods of obtaining a recombinant mammalian cell with a high volumetric productivity, or yield, of a polypeptide of interest can comprise selecting a cell that has a high volumetric productivity, or yield, of a polypeptide of interest when grown in a chemically defined medium, free of animal-derived components. A variety of media free of animal-derived components are commercially available, and can be selected based on the type of mammalian cell to be used. For example, CHO cells can be cultured in media such as CD-DG44 and CD OptiCHO™ (Invitrogen) supplemented with ZAP-CHO® (InVitria), and NS0 cells can be cultured in media such as EX-CELL® NS0 Serum-free medium (Sigma-Aldrich).

4.4. Use of Recombinant Mammalian Cells

The recombinant mammalian cells described herein are useful for producing polypeptides of interest. Accordingly, the present disclosure provides method for producing a polypeptide of interest, comprising culturing a recombinant mammalian cell under conditions that result in expression of the polypeptide of interest. Optionally, the method further comprises additional steps, which can include recovering the polypeptide and purifying the polypeptide.

Recombinant mammalian cells may be cultured in suspension, either by static culture or by shaking cultivation in flasks, or small-scale or large-scale fermentation (including continuous, batch, fed-batch, or solid state cultivation) in laboratory or industrial bioreactors performed in a suitable medium and under conditions allowing the polypeptide of interest to be expressed and/or isolated.

Techniques for recovering and purifying expressed protein are well known in the art and can be tailored to the particular polypeptide(s) being expressed by the recombinant mammalian cell. Polypeptides can be recovered from the culture medium and/or cell lysates. In embodiments where the method is directed to producing a secreted polypeptide, the polypeptide can be recovered from the culture medium. Polypeptides may be recovered or purified from culture media by a variety of procedures known in the art including but not limited to, centrifugation, filtration, extraction, spray-drying, evaporation, or precipitation. The recovered polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCU Publishers, New York, 1989).

5. EXAMPLE

Example 1: Mammalian Cells Stably Transfected with Expression Vectors Bearing Selectable Markers Under the Control of dESV40 Promoter Show Increased Yield as Compared to Vectors with a wtSV40 Promoter This example demonstrates that expression vectors containing a dESV40 promoter, instead of wtSV40 promoter, operably linked to a selectable marker, can be used to generate stably transfected recombinant mammalian cells with high yield of a polypeptide of interest.

Vectors.

A series of expression vectors was made to test the effect of using a dESV40 promoter as compared to a wtSV40 promoter on the ability to recover high yield transfected mammalian cells.

Vectors pV1.dESV40.X and pV1.wtSV40.X, depicted in FIGS. 2C-D, contain a selectable marker (DHFR or E. coli gpt) under the control of either the dESV40 promoter shown in FIG. 1 or wild type SV40 promoter (Reddy et al., 1978, Science 200:494-502), and an expression cassette comprising a first and second polypeptide coding sequence, each under the control of a mammalian viral promoter (expression promoter 1).

Vectors were constructed to express one of five test antibodies, Ab1 through Ab5, or a dual-variable domain immunoglobulin, DVD1. Vectors contain gene sequences encoding heavy and light chain polypeptides for each of Ab1, Ab2, Ab3, Ab4, Ab5, and DVD1. The vectors also include a polyadenylation sequence (pA) downstream of the selectable marker coding sequence and each polypeptide coding sequence. An ampicillin resistance marker (AMP) and bacterial origin of replication were used for cloning and propagating the vector in bacteria. Vectors are named to reflect the identity of the SV40 promoter tested (dESV40 or wtSV40) and the protein produced (X is Ab1, Ab2, Ab3, Ab4, Ab5, or DVD1). For example, a vector containing the dESV40 promoter and expressing Ab1 is named pV1.dESV40.Ab1.

Vectors pV2.dESV40.DVD1 and pV2.wtSV40.DVD1, depicted in FIGS. 2E-F, contain a selectable marker (DHFR) under the control of either the dESV40 promoter shown in FIG. 1 or wild type SV40 promoter (Reddy et al., 1978, Science 200:494-502), and cDNA sequences encoding heavy and light chain polypeptides of the test dual variable domain immunoglobulin, DVD1, under the control of a mammalian viral promoter. The vectors also include a polyadenylation sequence (pA) downstream of the selectable marker coding sequence and each polypeptide coding sequence. An ampicillin resistance marker (AMP) and bacterial origin of replication were used for cloning and propagating the vector in bacteria. Vectors are named to reflect the identity of the SV40 promoter tested (dESV40 or wtSV40).

Growth Media.

Culture media used for transfection, selection, and yield assays were suited to the mammalian cell type and the selectable marker. Suitable media for NS0 cells transfected with gpt-containing expression vectors are commercially available, e.g., EX-CELL® NS0 Serum-free medium (Sigma-Aldrich) and described in Hartman et al., 2007, Biotech Bioeng. 96:294-306. Suitable media for CHO cells transfected with DHFR-containing expression vectors are commercially available, e.g., chemically defined CHO media CD-DG44 and CD OptiCHO™ (Invitrogen), and described in the art, e.g., Zhang et al., 1995, Bio/Technology 13:389-392. In some experiments, the media used for selecting transfectants were supplemented with ZAP-CIO® (InVitria).

Transfection, Selection, and Screening.

As shown in FIG. 3, mammalian host cells were transfected and plated in 96-well plates, in suspension culture, at a density of 20,000 to 30,000/well, followed by selection in chemically defined medium, with the appropriate selection reagent (e.g., medium without hypoxanthine and thymidine, with or without methotrexate for DHFR, and medium with mycophenolic acid for xanthine guanine phosphoribosyl transferase). Selection was performed in 96-well plates using conditions that yield single colonies which maintains diversity and reduces isolation of multiple sibling clones.

For transfection with DHFR-containing vectors, the amount of methotrexate used was titrated to achieve single colonies in the 96-well plates. pV1.dESV40.DVD1 transfectants were selected in medium lacking hypoxanthine and thymidine (HT⁻) without methotrexate. pV2.dESV40.DVD1 transfectants were selected in HT⁻ medium with 25 nM methotrexate. pV2.wtSV40.DVD1 transfectants were selected in HT⁻ medium with 200 nM methotrexate. pV1.dESV40.Ab1 and pV1.dESV40.Ab2 transfectants were selected in HT⁻ medium without methotrexate and pV1.wtSV40.Ab1 transfectants were selected in HT⁻ medium with 50 nM methotrexate.

Resistant colonies from one or more transfections were screened within ten to twenty days of transfection using ELISA to measure polypeptide expression levels in the 96-well plates and positive clones were expanded in chemically defined medium with or without selection reagent followed by a 24-hour assay for protein yield, using methods described in Hartman et al., 2007, Biotech Bioeng. 96:294-306. Briefly, sandwich ELISA was performed to detect immunoglobulin expression from transfectant colonies using antibodies against human IgG Fc and human kappa light chain (Biosource, Camarillo, Calif.). The 24-h protein yield assay was performed in a 12-well plate by seeding $1 \times 10^6$ viable cells/mL in 1 mL of chemically defined medium and incubating at 37° C., 7.5% $CO_2$, for 24 h. The antibody concentration in the assay supernatant was determined by HPLC using a Protein A column. No amplification or further rounds of selection were performed after this initial screening. Positive transfectants that showed high yield were banked. Cell lines exhibiting highest yields can be re-screened in a fed-batch process in shake flasks.

The entire process for generating mammalian cell lines capable of expressing high levels of a polypeptide of interest can be completed in 6 to 8 weeks and does not require a step of gene amplification or subcloning.

Expression vectors were tested in three different mammalian cell types: the murine myeloma NS0 cell line and two DHFR⁻ CHO cell lines adapted to growth in suspension culture, CHO DG44 and CHO DXB11.

Results.

The effectiveness of the dESV40 promoter, as compared to wtSV40 promoter was demonstrated with two different polypeptides of interest, in two different expression vectors. First, vectors pV1.dESV40.DVD1 and pV2.dESV40.DVD1 were compared to pV2.wtSV40.DVD1. Each vector was transfected into CHO cell line DXB11, selected for DHFR expression, and screened in the 24-hour assay for DVD1 production. As shown in FIG. 4A, mammalian cells transfected with two different expression vectors, pV1.dESV40.DVD1 or pV2.dESV40.DVD1, containing the dESV40 promoter were capable of producing up to 35 to 38 µg/mL of the test dual variable domain immunoglobulin (DVD1). In contrast, the control vector containing the wild type SV40 promoter, pV2.wtSV40.DVD1, only yielded transfectants producing less than 10 µg/mL DVD1, demonstrating the effectiveness of the dESV40 promoter-containing expression constructs. Second, vectors pV1.dESV40.Ab1 and pV1.wtSV40.Ab1, were compared. Each vector was transfected into CHO DG44 cells transfected, selected for DHFR expression, and screened for expression of test antibody Ab1 in 96-well plates. As shown in FIG. 4B, the average antibody titer in colonies screened in 96-well plates was almost 14 µg/mL for the transfectants bearing the dESV40-containing construct as compared to less than 4 µg/mL for transfectants bearing the control wtSV40-containing construct. Furthermore, 19 (or 19%) of the pV1.dESV40.Ab1 transfectants had an antibody titer of more than 20 µg/mL, whereas there were only 6 (or 3%) of the pV1.wtSV40.Ab1 transfectants with an antibody titer of more than 20 µg/mL.

The usefulness of dESV40-containing expression vectors expressing test polypeptides in mammalian host cells was confirmed by transfecting CHO DG44 and DXB11 cells and murine myeloma NS0 cells with vectors expressing two different test polypeptides, Ab1 and Ab2. As shown in FIGS. 5A-B, pV1.dESV40.Ab1 and pV1.dESV40.Ab2 generated recombinant mammalian cells capable of producing up to 40 µg/mL of a test antibody and averaging over 10 µg/mL for Ab1 (FIG. 5A), and about 4 to 5 µg/mL for Ab2 (FIG. 5B), in NS0, DG44, and DXB11 cells as measured using the 24-hour protein yield assay.

DXB11 cell lines with the highest yield in the 24-hour protein assay were further tested in shake flasks under fed-batch conditions, and the results are shown in the Table below.

TABLE 1

| Host | Clone ID | 24 Hr (µg/mL) | Fed-batch Performance | | |
|---|---|---|---|---|---|
| | | | QAb (pg/cell/day) | IVCC ($10^9$c*d/L) | Final Titer (g/L) |
| DXB11 | Ab2-E10 | 12.8 | 13.6 | 61.7 | 0.84 |
| | Ab2-E12 | 13.4 | 14.8 | 59.6 | 0.89 |
| | Ab1-F13 | 18.8 | 19.6 | 89.3 | 1.75 |
| | Ab1-F3 | 21.6 | 16.4 | 75.3 | 1.24 |
| | Ab1-F19 | 22.0 | 22.4 | 54.1 | 1.21 |
| | Ab1-F16 | 27.0 | 19.5 | 96.9 | 1.89 |
| | Ab1-F11 | 39.6 | 29.7 | 42.5 | 1.26 |

As shown in the table, transfected DXB11 cells were identified that were capable of producing from about 0.9 to about 1.9 g/L, or about 13 to about 30 pg/cell/day, of the test antibody, demonstrating the ability to use the expression vectors to generate high yield transfectants.

In a further experiment, production of three additional antibodies was tested in NS0 cells transfected with pV1.dESV40.Ab3, pV1.dESV40.Ab4, or pV1.dESV40.Ab5, in which the selectable marker was gpt. At least one NS0 cell line transfected with a pV1.dESV40.Ab4 vector had antibody yields ranging as high as 31 to 40 mg/L in the 24-hour assay, and 8 cell lines had antibody yields as high as 21 to 30 mg/L (2 with pV1.dESV40.Ab3, and 3 each with pV1.dESV40.Ab4 and pV1.dESV40.Ab5). 35 NS0 cell lines showed antibody yields ranging from 11 to 20 mg/L.

Applicants have also identified optimized selection conditions that generated higher yielding CHO transfectants expressing Ab1 or Ab2, using selection media containing supplements. FIG. 6 shows that CHO cells transfected with pV1.dESV40.Ab1 or pV1.dESV40.Ab2, subjected to selection in the presence of ZAP-CHO® supplement produced higher levels of the test antibody than recombinant mammalian cells selected in the absence of ZAP-CHO supplement.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A Chinese hamster ovary (CHO) cell stably transfected with a vector, wherein the vector comprises:
   (i) an expression cassette, where the expression cassette comprises a first polynucleotide sequence encoding a first polypeptide of interest operably linked to a first expression promoter capable of effecting expression of the first polypeptide in the cell; and
   (ii) a polynucleotide sequence encoding a selectable marker operably linked to a portion of the SV40 promoter, wherein the portion of the SV40 promoter consists of only 206 consecutive nucleic acids of the wild type SV40 promoter; the 206 consecutive nucleic acids having the sequence of SEQ ID NO:1, and wherein the selectable marker is dihydrofolate reductase (DHFR).

2. The cell of claim 1, in which the expression cassette further comprises a second polynucleotide sequence encoding a second polypeptide of interest operably linked to a second expression promoter capable of effecting expression of the second polypeptide in the cell.

3. The cell of claim 2, in which the first and second expression promoters are the same.

4. The cell of claim 2, in which the first and the second expression promoters are selected from the group consisting of: Rous sarcoma virus (RSV) promoter, cytomegalovirus immediate early (CMV IE) promoter, cytomegalovirus major intermediate-early (MIE) promoter, simian virus 40 (SV40) early promoter, Adenovirus major late promoter (AML), mouse mammary tumor virus LTR promoter, Herpes thymidine kinase promoter, human β-actin (ACTB) promoter, elongation factor-1α (EF1α) promoter, the phosphoglycerate kinase (PGK) promoter, the ubiquitinC (UbC) promoter, and murine metallothionein promoter.

5. The cell of claim 1, in which the expression cassette further comprises a second polynucleotide sequence encoding a second polypeptide, 3' to the first polynucleotide sequence.

6. The cell of claim 5, in which the first promoter is selected from the group consisting of: Rous sarcoma virus (RSV) promoter, cytomegalovirus immediate early (CMV IE) promoter, cytomegalovirus major intermediate-early (MIE) promoter, simian virus 40 (SV40) early promoter, Adenovirus major late promoter (AML), mouse mammary tumor virus LTR promoter, Herpes thymidine kinase promoter, human β-actin (ACTB) promoter, elongation factor-1α (EF1α) promoter, the phosphoglycerate kinase (PGK) promoter, the ubiquitinC (UbC) promoter, and murine metallothionein promoter.

7. The cell of claim 6, in which the first promoter is cytomegalovirus immediate early (CMV 1E) promoter.

8. The cell of claim 5, comprising an internal ribosome entry site (IRES) between the first and second polynucleotide sequences.

9. The cell of claim 1, further comprising an enhancer element operably linked 5' to the expression promoter.

10. The cell of claim 1, which is capable of producing at least 0.5 g/L of the polypeptide of interest in a 10-day fed batch culture.

11. The cell of claim 1, which is capable of producing at least 10 pg/cell/day of the polypeptide of interest in a 10-day fed batch culture.

12. A Chinese hamster ovary (CHO) cell stably transfected with a vector useful for effecting expression of an antibody of interest, wherein the vector comprises:
   (i) an expression cassette, where the expression cassette comprises a first polynucleotide sequence encoding a heavy chain of an antibody of interest, operably linked to a first expression promoter capable of effecting expression of the encoded heavy chain in the cell, and a second polynucleotide sequence encoding a light chain of an antibody of interest, operably linked to a second expression promoter capable of effecting expression of the encoded light chain in the cell; and
   (ii) a polynucleotide sequence encoding a selectable marker operably linked to a portion of the SV40 promoter, wherein the portion of the SV40 promoter consists of only 206 consecutive nucleic acids of the wild type SV40 promoter; the 206 consecutive nucleic acids having the sequence of SEQ ID NO:1, and wherein the selectable marker is dihydrofolate reductase (DHFR).

13. The cell of claim 12, in which the first and second expression promoters are the same and are selected from the group consisting of: Rous sarcoma virus (RSV) promoter, cytomegalovirus immediate early (CMV IE) promoter, cytomegalovirus major intermediate-early (MIE) promoter, simian virus 40 (SV40) early promoter, Adenovirus major late promoter (AML), mouse mammary tumor virus LTR promoter, Herpes thymidine kinase promoter, human β-actin (ACTB) promoter, elongation factor-1α (EF1α) promoter, the phosphoglycerate kinase (PGK) promoter, the ubiquitinC (UbC) promoter, and murine metallothionein promoter.

14. The cell of claim 13, in which the first and second expression promoters are cytomegalovirus immediate early (CMV 1E) promoters.

15. A method of obtaining a Chinese hamster ovary (CHO) cell capable of producing a polypeptide of interest in high yield in culture, comprising transfecting a CHO cell of claim 1, and selecting the cell that is capable of producing at least 10 pg/cell/day of the polypeptide of interest in a 10-day fed batch culture.

16. The method of claim 15, in which the cell is not subjected to amplification.

17. A method for producing a polypeptide of interest, comprising culturing the cell of claim 1.

18. The method of claim 17, wherein the cell is cultured under conditions that result in the production of at least 10 pg/cell/day of the polypeptide of interest in a 10-day fed batch culture.

19. The method of claim 17, wherein the cell is cultured under conditions that result in the production of at least 0.5 g/L of the polypeptide of interest in a 10-day fed batch culture.

* * * * *

SEQUENCE LISTING

```
<160> NUMBER OF SEQ ID NOS: 1

<210> SEQ ID NO 1
<211> LENGTH: 206
<212> TYPE: DNA
<213> ORGANISM: Artificial Sequence
<220> FEATURE:
<223> OTHER INFORMATION: "Description of Artificial Sequence:  Synthetic
      Polynucleotide"

<400> SEQUENCE: 1
gcatgcatct caattagtca gcaaccatag tcccgcccct aactccgccc atcccgcccc       60
taactccgcc cagttccgcc cattctccgc cccatggctg actaattttt tttatttatg      120
cagaggccga ggccgcctcg gcctctgagc tattccagaa gtagtgagga ggcttttttg      180
gaggcctagg cttttgcaaa aagctt                                           206
```